(12) United States Patent
Horseman et al.

(10) Patent No.: US 9,585,870 B2
(45) Date of Patent: Mar. 7, 2017

(54) COMPOSITIONS AND METHODS FOR IMPROVING LACTATION

(71) Applicant: UNIVERSITY OF CINCINNATI, Cincinnati, OH (US)

(72) Inventors: Nelson Horseman, Cincinnati, OH (US); Laura Hernandez Baumgard, Madison, WI (US)

(73) Assignees: UNIVERSITY OF CINCINNATI, Cincinnati, OH (US); WISCONSIN ALUMNI RESEARCH FOUNDATION, Madison, WI (US)

( * ) Notice: Subject to any disclaimer, the term of this patent is extended or adjusted under 35 U.S.C. 154(b) by 24 days.

(21) Appl. No.: 14/375,103

(22) PCT Filed: Jan. 25, 2013

(86) PCT No.: PCT/US2013/023196
§ 371 (c)(1),
(2) Date: Jul. 28, 2014

(87) PCT Pub. No.: WO2013/112873
PCT Pub. Date: Aug. 1, 2013

(65) Prior Publication Data
US 2015/0031741 A1    Jan. 29, 2015

Related U.S. Application Data

(60) Provisional application No. 61/591,009, filed on Jan. 26, 2012.

(51) Int. Cl.
*A61K 31/405* (2006.01)

(52) U.S. Cl.
CPC .......... *A61K 31/405* (2013.01); *A23K 20/142* (2016.05); *A23K 40/35* (2016.05); *A23K 50/10* (2016.05); *A23K 50/30* (2016.05); *A23K 50/75* (2016.05); *A23L 33/175* (2016.08); *A23V 2002/00* (2013.01)

(58) Field of Classification Search
CPC .................................................... A61K 31/405
USPC ....................................................... 514/419
See application file for complete search history.

(56) References Cited

U.S. PATENT DOCUMENTS

| 7,241,797 B2 * | 7/2007 | Horseman | ............ | A61K 31/405 514/412 |
| 8,133,916 B1 * | 3/2012 | Horseman | ............ | A61K 31/135 514/555 |

* cited by examiner

*Primary Examiner* — San-Ming Hui
(74) *Attorney, Agent, or Firm* — Jenei LLC; Stephen Jenei (57) ABSTRACT

The present disclosure relates to the use of pharmaceutical agents to manipulate serotonin in animal mammary glands. Use of the serotonin agents results in increased PTHrP levels, resulting in the release of calcium from the bone, which improves lactation.

19 Claims, 1 Drawing Sheet

COMPOSITIONS AND METHODS FOR IMPROVING LACTATION

CROSS REFERENCE TO RELATED APPLICATIONS

This application claims the benefit of U.S. Provisional Patent Application 61/591,009, entitled "Mammary Gland Serotonin Regulates Parathyroid Hormone-Related Protein and Other Bone-Related Signals" filed Jan. 26, 2012, and PCT Application PCT/US13/23196, entitled "Compositions And Methods For Improving Lactation" filed Jan. 25, 2013, the entire contents of which applications are incorporated herein by reference.

STATEMENT REGARDING FEDERALLY SPONSORED RESEARCH OR DEVELOPMENT

This research was made possible by funding from the NRI Competitive Grant 02008-35206-17898 from the USDA. The government may have certain rights in this invention.

BACKGROUND OF THE INVENTION

1. Field of the Invention

The present disclosure relates to the use of pharmaceutical agents to manipulate serotonin in animal mammary glands. Use of the serotonin agents results in increased PTHrP levels, resulting in the release of calcium from the bone, which improves lactation.

2. Description of the Related Art

The transition from pregnancy to lactation in mammals is a critical period for calcium homeostasis. Approximately 5% of all dairy animals experience severe periparturient hypocalcemia, also known as milk fever. This number increases to approximately 50% in older cows, and the highest-producing cows are at highest risk of this pathology. At calving, there is a 4-5% increase in plasma calcium clearance, with calcium replacement coming from the mobilization of calcium from bone. Similar bone calcium mobilization occurs in human women during the periparturient period.

The specific mobilization of bone in lactation is driven by a hormone named "Parathyroid Hormone-related Protein (PTHrP, gene symbol PTHLH, also known as HHM; PLP; BDE2; PTHR; PTHRP)." A failure to maintain calcium homeostasis during the transition to milk secretion is at the heart of periparturient hypocalcemia.

PTHrP was originally discovered as the factor responsible for humoral hypercalcemia of malignancy, and is secreted from a variety of advanced soft tissue cancers. The N-terminal portion of PTHrP is similar to parathyroid hormone (PTH), and acts via the type 1 PTH receptors (PTH1R) to induce the receptor-activator of NFKB ligand (RANKL).

PTHrP is undetectable in the circulation except during lactation, in advanced metastatic disease, or in patients with hyperprolactinemia. In spite of obvious correlations with states of elevated prolactin (PRL), PRL did not induce PTHrP in conventional cell cultures of mammary epithelium, and our lab has done numerous experiments that confirmed that PRL does not induce PTHrP in mammary cells by a direct mechanism.

A previous study showed that serotonin (5-HT) induced PTHrP expression in vascular smooth muscle cells. In the mammary glands 5-HT regulates key aspects of epithelial homeostasis by autocrine-paracrine signaling. The processes regulated by 5-HT include not only specialized mammary gland functions such as milk protein and milk lipid biogenesis, but also fundamental cell biological processes (i.e., apoptosis, barrier permeability, cell shedding). Epithelia lining other ductal/alveolar secretory organs also possess local 5-HT signaling systems, which have been implicated in various aspects of epithelial homeostasis.

It has now been shown that serotonin, synthesized within the mammary gland, is responsible for causing the increase in PTHrP associated with the onset of lactation. Consequently, drugs that increase serotonin signaling are useful for maintaining healthy calcium levels in lactating females.

SUMMARY OF THE INVENTION

In one aspect, the present disclosure provides for methods and compositions for promoting calcium mobilization.

In another embodiment, the present invention provides for the use of pharmacological agents that are able to promote calcium mobilization, and which therefore prevent or treat conditions that are common in mammals, including dairy cattle and human females, at the onset of lactation.

In one embodiment of the present invention, there is provided the use of serotonin agonist, a salt thereof or a composition containing serotonin agonist or a salt thereof for improving calcium mobilization of lactating animals.

In another embodiment of the present invention, there is provided a feed for improving calcium mobilization of lactating animals comprising a composition containing serotonin agonist or a salt thereof and a stabilizer.

In another embodiment of the present invention, there is provided a method for improving calcium mobilization of lactating animals comprising steps of producing a final feed by mixing a composition containing serotonin agonist or a salt thereof and a stabilizer with a suitable premix, which is a component of the final feed for animals.

Another aspect of the invention is the use of a serotonin agonist in the manufacture of a medicament to increase ruminant serum calcium concentrations, and to increase ruminant milk quality and/or milk yield.

The present invention provides the use of 5-HTP in the manufacture of a medicament to increase calcium mobilization in a ruminant animal.

The present invention provides the use of 5-HTP in the manufacture of a medicament to increase lactation in a ruminant animal.

One aspect of the invention provides for the use of 5-HTP in the manufacture of a medicament for the palliative, prophylactic or curative treatment of ruminant diseases associated with reduced calcium concentrations.

In another specific embodiment, the overall increase in ruminant milk yield, or the increase in peak milk yield, or the increase in milk quality, is obtained from a dairy cow.

In one aspect of the invention, the increase in ruminant milk quality and/or milk yield is obtained after administration of a serotonin agonist to a healthy ruminant.

In another aspect of the invention, there is provided a serotonin agonist for increasing ruminant serum calcium concentration in the periparturient period.

In one embodiment, the present invention provides for the use of a serotonin agonist in the manufacture of a medicament to increase ruminant serum calcium concentrations, wherein the deficiencies of calcium levels in serum is prevented or alleviated.

In another embodiment, the present invention provides for the use of a serotonin agonist in the manufacture of a medicament for the palliative, prophylactic or curative treatment of ruminant diseases associated with reduced serum calcium concentrations, wherein periparturient hypocalcemia or milk fever, is prevented or alleviated.

The improved calcium mobilization may also produce an increase in milk yields, fat-corrected milk yields, milk fat content therein and/or milk protein content therein.

In one embodiment, the composition comprises substantially 1-95 wt % serotonin agonist. In particular, the composition may comprise substantially 5-30 wt % serotonin agonist.

In one embodiment, the composition comprises substantially 1 to 80 wt % of the stabilizer. The stabilizer is preferably selected from a group including cyclodextrin or a derivative thereof. In particular, the composition may comprise substantially 10 wt % of the stabilizer.

In one embodiment, the composition further comprises ingredient(s) selected from a group including a bulking agent, a disintegration agent and a coated carrier. In one embodiment, the coated carrier in some embodiments is a solid carrier, which is a coating soluble in intestines of the animals. The coated carrier suitably exhibits a multi-layer structure in the composition. The coated carrier is preferably adapted to remain undissolved at pH 1.5 to 3.5.

In some embodiments, the feed comprises other foodstuffs selected from a group including normal premix, cornmeal, cotton seed, wheat gluten, maize silage rutabaga, sugar beet pulp, apple pulp, ryegrass, fescue grass, alfalfa, feed concentrate and feed supplement.

The mention of use of compounds in the present invention, shall at all times be understood to include all active forms of such compounds, including, for example, the free form thereof, e.g., the free acid or base form, and also, all prodrugs, polymorphs, hydrates, solvates, tautomers, stereoisomers, e.g., diastereomers and enantiomers, and the like, and all pharmaceutically acceptable salts as described above, unless specifically stated otherwise. It will also be appreciated that the use of suitable active metabolites of such compounds, in any suitable form, are also included herein.

This invention makes use of stimulation of PTHrP by serotonin agonist compounds during the period of sensitivity to hypocalcemia. The invention is a method to administer serotonergic agents, such as a receptor agonist, releasing agent, reuptake inhibitor, inhibitor of degradation, or precursor chemical, with the intent and ultimate consequence that extraction of calcium from bone is accelerated. The person will administer (such as by intra-mammary infusion, injection, or feeding, a serotonergic agents) at a predetermined dose so as to activate calcium mobilization and prevent, or treat, periparturient hypocalcemia.

These and other features are explained more fully in the embodiments illustrated below. It should be understood that in general the features of one embodiment also may be used in combination with features of another embodiment and that the embodiments are not intended to limit the scope of the invention.

BRIEF DESCRIPTION OF THE DRAWINGS

The various exemplary embodiments of the present invention, which will become more apparent as the description proceeds, are described in the following detailed description in conjunction with the accompanying drawings, in which.

DETAILED DESCRIPTION

It is to be understood that other embodiments may be utilized and changes may be made without departing from the scope of the present invention. Also, it is to be understood that the phraseology and terminology used herein are for the purpose of description and should not be regarded as limiting. The use of "including," "comprising," or "having" and variations thereof herein is meant to encompass the items listed thereafter and equivalents thereof as well as additional items.

Abbreviations used are TPH1: tryptophan hydroxylase 1; 5-HT: serotonin; PTHrP: parathyroid hormone-related peptide (a.k.a. parathyroid hormone-like hormone). 5-Hydroxytryptophan (5-HTP), also known as oxitriptan (INN), is a naturally occurring amino acid and chemical precursor as well as a metabolic intermediate in the biosynthesis of the neurotransmitters serotonin and melatonin from tryptophan.

As used in this specification and the appended claims, the singular forms "a", "an" and "the" can include plural references unless the content clearly dictates otherwise. Thus, for example, reference to "a component" can include a combination of two or more components; a reference to "containers" can include individual containers, and the like.

Although many methods and materials similar, modified, or equivalent to those described herein can be used in the practice of the present invention without undue experimentation, the preferred materials and methods are described herein. In describing and claiming the present invention, the following terminology will be used in accordance with the definitions set out below.

As used herein the terms "administer", "administered", and "administration" of the various substances (e.g., 5-HTP) denote providing an additional amount of the substance into the animal's bloodstream on the indicated days, whether via daily or other injections on those days or by release on those days from a parenterally administered prolonged release delivery system (e.g., pellet, liquid depot, vaginal suppository or the like), or by continuous dosing (e.g., by an infusion pump) of the substance, delivered parenterally at the beginning of the time period, or, in the case of the continuous dose, throughout the time period. Alternatively it may refer to the delivery of the dosage by periodic (e.g. daily) parenteral injection or implantation or the like.

The term "animal" is used herein to include all vertebrate animals, including humans. It also includes an individual animal in all stages of development, including embryonic and fetal stages. As used herein, the term "production animals" is used interchangeably with "livestock animals" and refers generally to animals raised primarily for food. For example, such animals include, but are not limited to, cattle (bovine), sheep (ovine), pigs (porcine or swine), poultry (avian), and the like.

The term "effective amount", as used herein, refers to an amount of specified material adequate to provide a desired effect. For example, an effective amount of a supplemental constituent in compositions of the present invention can be an amount adequate to pass through the rumen to the post rumen digestive tract for provision of a desired effect. Desired effects can include, e.g., improved calcium mobilization, nutrition and health for the ruminant, pharmaceutical effects, effects on the composition of meat or milk, effects on the productivity of meat or milk, and/or the like.

As used here and, the term "lactation" means the production of milk and/or or secretion of milk by the mammary glands of a mammal or the period following giving birth during which milk is secreted in the breasts of a mammal.

As used herein, the term "mammal" means the Mammalia class of higher vertebrates. The term "mammal" includes, but is not limited to, a human. In one embodiment, the mammal is a ruminant animal.

As used herein, the term "ruminant" means an even-toed hoofed animal that has a complex 3-chamber or 4-chamber stomach and which typically re-chews what it has previously swallowed. Some non-exhaustive examples of ruminants include cattle, sheep, goats, oxen, muskox, llamas, alpacas, guanicos, deer, bison, antelopes, camels, and giraffes.

The term "lipid", as used herein, refers, e.g., to any oil, fat, or substantially hydrophobic organic material. Lipid droplets or lipid particles in the filler composition or dispersed phase can include, e.g., oils, fats, monoglycerides, diglycerides, triglycerides, free fatty acids; corn oil, poppy seed oil, fish oil, cotton seed oil, soybean oil, walnut oil, safflower oil, sunflower oil, sesame oil, canola oil, linseed oil; free, esterified, or conjugated: oleic acid, linoleic acid, linolenic acid, phytanic acid, omega 3 fatty acids, eicosapentaenoic acid; lipid-containing materials, such as whole or modified oil seed or beans (such as soybeans), grape seeds, cotton seeds, safflower seeds; algae, microorganisms, yeasts, protozoa, etc.; and/or the like.

The term "pharmaceutically" or "pharmacologically acceptable", as used herein, refer to molecular entities and compositions that do not produce adverse, allergic, or other untoward reactions when administered to an animal or a human.

The term, "pharmaceutically acceptable carrier", as used herein, includes any and all solvents, or a dispersion medium including, but not limited to, water, ethanol, polyol (for example, glycerol, propylene glycol, and liquid polyethylene glycol, and the like), suitable mixtures thereof, and vegetable oils, coatings, isotonic and absorption delaying agents, liposome, commercially available cleansers, and the like. Supplementary bioactive ingredients also can be incorporated into such carriers.

The term "supplemental constituents" or "supplementary bioactive ingredients", as used herein, refers to constituents of a composite gel for protection through the rumen. Supplemental constituents can be present in the dispersed phase and/or the continuous phase of the composite gel. Certain supplemental constituents can play a role in the lipid or protein matrix structure of the composite gel. Optionally, supplemental constituents are carried and protected by the lipid and/or matrix structure of the composite gel. Supplemental constituents can include, e.g., polyunsaturated fatty acids, monounsaturated fatty acids, free and esterified fatty acids, amino acids, proteins, pharmaceuticals, bioactive agents, nutrients, minerals, vitamins, antibiotics, and/or the like.

Other constituents, such as supplemental constituents, plasticizers, emulsifiers, stabilizers, anti-oxidants, redox-potential modifiers, minerals, texture modifiers, thickening agents, etc., can range, e.g., from about zero percent to about 20 percent or more of the total suspension solids by weight. Such components can be, but are not limited to, materials such as natural or modified gums that are permitted for utilization in feed and food preparations, starches, modified starches, dextrins, maltodextrins, etc. Supplemental constituents that can be added to the matrix suspension include, e.g., vitamins, nutrients, amino acids, peptides, minerals, hormones, bioactive materials, bioengineered compounds, pharmaceuticals, and/or the like.

As used herein, the terms "rumen-bypass," "rumen-inert," and rumen-protected," when used to characterize a substance, such as fat, protein, carbohydrate, etc., means the substance is naturally-resistant, to some degree, to alteration during passage of the rumen-bypass substance through the rumen of a ruminant and/or means the substance has been processed, treated, or associated with another material in some fashion that protects, to some degree, the rumen-bypass substance from alternation during passage of the rumen-bypass substance through the rumen of a ruminant.

As used herein, "therapeutically effective amount of a compound" means an amount that is effective to exhibit therapeutic or biological activity at the site(s) of activity in a ruminant, without undue adverse side effects (such as undue toxicity, irritation or allergic response), commensurate with a reasonable benefit/risk ratio when used in the manner of the present invention.

It is not intended that the present invention be limited by the particular nature of the therapeutic preparation. The serotonin agonist can be prepared in any type of appropriate medium for administration. For example, the serotonin agonist can be provided together with physiologically tolerable liquid (e.g., saline), gel or solid carriers, diluents, adjuvant, excipients and as a rumen-protected encapsulated ingredient. Suitable diluents and excipients include pharmaceutical grades of physiological saline, dextrose, glycerol, mannitol, lactose, starch, magnesium stearate, sodium saccharin, cellulose, magnesium carbonate, and the like, and combinations thereof. In addition, if desired the compositions may contain minor amounts of auxiliary substances such as wetting or emulsifying agents, stabilizing or pH buffering agents. These compositions typically contain 1%-95% of active ingredient, preferably 2%-70%. The serotonin agonist can be incorporated into tablets, boluses, or capsules, and dosed to the patient. The serotonin agonist may also be incorporated into salt blocks and the like. The serotonin agonist can be added to feed as a freeze-dried powder or as an encapsulated composition that is protected from degradation in the rumen. In one embodiment, the serotonin agonist is prepared in a solution of physiological phosphate-buffered saline (PBS) or for oral administration to a ruminant.

In one embodiment, the present invention provides for a method of treatment of a lactating mammal comprising the step of administering to the mammal a therapeutically effective amount of 5-hydroxytryptophan. In one embodiment, the effective daily dosages of 5-HTP can range between about 5 mg and about 10,000 mg (e.g., between about 5 mg and 10,000 mg, 25 mg and about 2000 mg, about 50 mg and about 2000 mg, about 50 mg and about 1500 mg). In some cases, an effective daily dose of 5-HTP can range between about 25 mg to about 2500 mg.

The serotonin agonist can be incorporated into tablets, drenches, boluses, capsules or premixes. Formulation of these active ingredients into such dosage forms can be accomplished by means of methods well known in the pharmaceutical formulation arts. See, for example, U.S. Pat. No. 4,394,377. (This patent, and all other references cited herein are hereby incorporated by reference.) Filling gelatin capsules with any desired form of the active ingredients readily produces capsules. If desired these materials can be diluted with an inert powdered diluent, such as sugar, starch, powdered milk, purified crystalline cellulose, or the like to increase the volume for convenience of filling capsules.

Conventional formulation processes can be used to prepare tablets containing the serotonin agonist. In addition to the active ingredients, tablets may contain a base, a disintegrator, an absorbent, a binder, and a lubricant. Typical bases include lactose, sugar, sodium chloride, starch and mannitol. Starch is also a good disintegrator as is alginic acid. Surface-active agents such as sodium lauryl sulfate and dioctyl sodium sulphosuccinate are also sometimes used. Commonly used absorbents include starch and lactose. Magnesium carbonate is also useful for oily substances. As a binder there may be used, for example, gelatin, gums, starch, dextrin, polyvinyl pyrrolidone and various cellulose derivatives. Among the commonly used lubricants are magnesium stearate, talc, paraffin wax, various metallic soaps, and polyethylene glycol.

Drenches are prepared most readily by choosing a saline-suspended form of the serotonin agonist, fragments thereof or active molecules secreted therefrom. A water-soluble form of one ingredient may be used in conjunction with a water-insoluble form of the other by preparing a suspension of one with an aqueous solution of the other. Water-insoluble forms of either active ingredient may be prepared as a suspension or in some physiologically acceptable solvent such as polyethylene glycol. Suspensions of water-insoluble forms of either active ingredient can be prepared in oils such as peanut, corn, sesame oil or the like; in a glycol such as propylene glycol or a polyethylene glycol; or in water depending on the solubility of a particular active ingredient. Suitable physiologically acceptable adjuvants may be necessary in order to keep the active ingredients suspended. The adjuvants can be chosen from among the thickeners, such as carboxymethylcellulose, polyvinyl pyrrolidone, gelatin and the alginates. Surfactants generally will serve to suspend the active ingredients, particularly the fat-soluble propionate-enhancing compounds. Most useful for making suspensions in liquid nonsolvents are alkylphenol polyethylene oxide adducts, naphthalenesulfonates, alkylbenzene-sulfonates, and the polyoxyethylene sorbitan esters. In addition many substances, which affect the hydrophilicity, density and surface tension of the liquid, can assist in making suspensions in individual cases. For example, silicone anti-foams, glycols, sorbitol, and sugars can be useful suspending agents.

Additionally the subject compositions of this invention may be separately administered, for example, by adding one directly to feed stuffs and co-administering the second material as a bolus tablet, drench, or capsule. Or each may be separately prepared and separately added to feed stuffs in appropriate quantities and at appropriate times. For example, such a material as choline stearate, a fatty acid complex, which may be used in the practice of this invention, may not be appropriate for incorporation into feed premixes because of its physical characteristics. In such an instance the choline stearate composition could be provided separately in a suitable diluent such as, for example, corn flour, ground corn cob, hominy, corn glutenmeal, wheat middlings, soybean meal, soybean mill feed, rice mill by-product, and the like and mixtures thereof. A description of such suitable diluents may be found in U.S. Pat. No. 4,394,377.

The serotonin agonist may be administered to an animal in a composition, a premix, that is then mixed into the animal feed supply. Such a composition may comprise the serotonin agonist alone or the serotonin agonist may be mixed with a carrier and/or with other drugs, vitamins, minerals, protein concentrates and similar feed supplements. These compositions may be prepared in dry granular powder form, as pellets, in the form of pastes, encapsulated to be rumen protected, or may be formulated as liquid feed supplements and the like. Any type of feed may be medicated with such compositions, including common dry feed, liquid feeds, and pelleted feeds. The methods of formulating supplemental materials into animal feeds are well known. It is necessary only to calculate the amount of each compound, which it is desired to administer to each animal, to take into account the amount of feed per day that the animal eats and then mix in the appropriate amount of the serotonin agonist. See U.S. Pat. No. 4,394,377.

The compositions of the invention may be used as a feed additive premix, feed additive concentrate or feed additive supplement in which the active ingredients are distributed uniformly throughout a standard organic or inorganic animal feed carrier in a concentrated form which is conveniently packaged and shipped to the feed mixer. The grower or the feed mixer then in turn mixes this premix, concentrate or supplement uniformly with a normal diet for the animal as desired. Examples of carriers for premix compositions are soybean meal, corn oil, ground corn, barley, wheat, mineral mixtures containing, e.g., vermiculite or diatomaceous earth, corn gluten meal, soy flour or other modestly priced edible ingredients.

The serotonin agonist may also be admixed with a suitable carrier such as an edible feed or feed component in the form of a feed additive supplement. Examples of such edible feed components are feed fortifiers and enhancers for preruminant bovine calves of any of the kinds disclosed in U.S. Pat. No. 6,156,333. If to be fed free choice or as a supplement, The serotonin agonist is provided according to the anticipated daily consumption of the supplement to provide a daily dose of each of these ingredients in one of the ranges specified.

In addition, the serotonin agonist may be incorporated directly into feeds by a mill or other feed supplier to provide a finished feed product to the grower. A finished feed product could be made up of any of the various grains, lucerne, grasses, minerals, vitamins, protein supplements, drugs and the like which go into the formulation of a nutritionally complete ruminant feed. The serotonin agonist may be mixed directly with cattle feed made up of various components such as hay, straw, silage, cornstalks, cottonseed hulls, grain, oats, barley and cereal brans, particularly for the ruminants; antioxidants, minerals, vitamins, anthelmintics, and other appropriate medicaments. See U.S. Pat. No. 4,394,377. Alternatively, The serotonin agonist may be incorporated into a liquid feed for preruminant bovine calves of any of the kinds disclosed in U.S. Pat. No. 6,156,333.

The serotonin agonist may be mixed into a suitable animal feed by any method appropriate for mixing a micronutrient or micro-component into animal feed. Examples of such methods include but are not limited to the following: spraying the serotonin agonist onto dry feed and mechanically mixing the serotonin agonist into dry or liquid feed; top dress grain or concentrate mix.

One of ordinary skill in the art will appreciate that the serotonin agonist may be administered in any manner consistent with the present invention. The serotonin agonist is typically given in an amount of approximately 50/kg mg to 500 mg/kg, with about 100 mg being preferable. The skilled artisan will appreciate that this amount of serotonin agonist can be delivered in a variety of ways and at a number of different dose levels (depending on the frequency of administration). In one embodiment the serotonin agonist is administered in a sustained-release formulation. In another embodiment, the serotonin agonist is administered to the animal until at least day 4 of the treatment, even more preferably until at least day 10 (e.g. on days 0, 2, 4, 6, 8, 10).

Those skilled in the art will also recognize that any natural or synthetic analog of 5-HTP having approximately the equivalent bioactivity of the 5-HTP native to the animal may also be used. Approximately equivalent bioactivity as used herein would be at least 50% of the bioactivity of the 5-HTP. Preferably such analog would have at least 75% of the equivalent bioactivity, more preferably 90% of the equivalent bioactivity and most preferably 100% or greater than 100% of the bioactivity equivalent to the 5-HTP.

The serotonin agonist-containing composition may also comprise 1 to 90 wt % of fillers although a preferable workable range of 1 to 60 wt % and a more preferable workable range of 1 to 40 wt % of the fillers may also be used in the composition. The actual content will depend on the actual amount of serotonin agonist and inclusion compound host materials used. The fillers may be selected from a group including powdered cellulose, starch and calcium sulfate (e.g. $CaSO_4.2H_2O$). It is to be noted that if the content of the fillers exceeds 90 wt % in the serotonin agonist-containing composition, the content of the main active ingredients will thus be reduced, and the serotonin agonist-containing composition may become ineffective in improving calcium mobilization of the animals fed with a feed mixed therewith.

The serotonin agonist-containing composition may also comprise 5 to 50 wt % of disintegrants and binders although a preferable workable range of 10 to 40 wt % and a more preferable workable range of 15 to 35 wt % may also be used. The actual content will depend on the actual amount of serotonin agonist, the inclusion compound host material and other ingredients used. The binders and disintegrants may be selected from a group including hydropropyl starch, microbial alginate, microcrystalline cellulose and starch. It has been identified that if the content of the disintegrants and binders in the composition is less than 5 wt %, granules of the composition produced will lack the required hardness. In addition, manufacturing of the composition would become very difficult. If however the content of the disintegrants and binders is more than 50 wt %, the resulting composition will have excessive hardness, this is especially so if the content of binders represent a large portion of the mixture of the disintegrants and binders. This will result in reduced absorption of the composition by the intestines of the animals.

The serotonin agonist-containing composition may also comprise 0.05 to 0.3 wt % of flavoring and smelling agents which may be a flavoring essence.

The serotonin agonist-containing composition may also comprise 1 to 20 wt % of coating materials although a preferable workable range is 1 to 15 wt % and a more preferable workable range is 2 to 10 wt %. The actual content will depend on the actual amount of serotonin agonist, the inclusion compound host materials and the other ingredients used. The coating materials are preferably enteric-coated which allows dissolution in an alkaline environment such as in the intestines. The coating materials may be made of and selected from a group including cellulose acetate phthalate, starch acetate phthalate, methyl cellulose phthalate, glucose or fructose derivatives from phthalic acid, acrylic and methacrylic copolymers, polymethyl vinyl ether, partly esterified substance of maleic anhydride copolymers, lac and formogelatine. It has been identified that if the content of the coating materials is less than 1 wt %, granules of the composition may not be entirely covered by the coating materials, which act as a protective layer. The serotonin agonist-containing composition may thus degrade before being absorbed by the intestines into the bloodstream of the animals. On the other hand, if the content of the coating materials exceeds 15 wt %, the active ingredients in the composition may not effectively be released from the composition. Thus, the intended regulation of calcium mobilization would not be achieved.

EXAMPLE 1

Materials and Methods $TPH1^{-/-}$, and corresponding wild type control animals (C57BL/6J genetic background) were bred and maintained in our animal facility. All experiments were performed under protocols approved by the University of Cincinnati Institutional Animal Care and Use Committee. Plasma was collected for PTHrP assay from non-lactating wild type mice and both wild type and $TPH1^{-/-}$ animals on day 10 of lactation. Mammary gland tissues (#4 glands counted from most rostral) were collected for immunostaining from $TPH1^{-/-}$ animals and wild type controls on day 10 of lactation, and were fixed in 4% paraformaldehyde, before being paraffin embedded and sectioned.

PTHrP IRMA. Plasma PTHrP levels were measured using a two-site immunoradiometric assay specific for PTHrP 1-86 (Becton Dickinson), following the manufacturer's instructions. The detection limit (blank serum+1 standard deviation) was 0.3 pM under the conditions of this assay.

Cell culture. Primary bovine mammary epithelial cells grown in collagen gels were induced to differentiate by release of the gel from the substratum, and treating with lactogenic hormones as described (15,31). The mouse mammary epithelial cells (HC11) were maintained under growth medium conditions, and lactogen-induced by treatment of 3 day confluent cultures with prolactin, insulin, and cortisol as previously described (17).

Primary bovine mammary epithelial cells (pBMEC) were obtained as a generous gift from Dr. Robert Collier at the University of Arizona and cultured as previously described (15,31).

Quantitative real-time RT-PCR amplification. Total RNA was isolated using TRIreagent® (Molecular Research) following manufacturer's procedures. RNA quality was determined through spectrophometric methods on the Nanodrop 2000 (Thermo Scientific). A total of 1 pg was reverse transcribed using the QuantiTect reverse transcription kit (Qiagen). Quantitative real-time RT-PCR was performed using the Applied Biosystems Step One Plus system (Applied Biosystems) using fast SYBR green master mix (Applied Biosystems). The following conditions were utilized: 95° C. for 20 sec. followed by 40 cycles of 95° C. for 3 sec., 60° C. for 30 sec.

Immunohistochemistry and western blotting. PTHrP fluorescent immunostaining was performed using a 1:50 dilution of goat anti-PTHrP (N-19; Santa Cruz Biotechnology) overnight at 4° C. and 1:1000 dilution of the rabbit anti-goat Alexa Fluor 488 Fa(b) fragments (Invitrogen) for 30 min at room temperature on paraffin-embedded sections of mammary gland tissue collected from $TPH1^{-/-}$ and wild type ($TPH1^{+/+}$) mice collected at day 10 of lactation. Nuclei were visualized using a 1:1000 dilution of TOPRO-3 (Invitrogen) for 20 min at room temperature. Fluorescence was visualized on a Zeiss LSM 10 confocal microscope.

Statistical Analyses. Statistical significance was determined in each experiment by Analysis of Variance (ANOVA), with Bonferroni's post-hoc test for relevant differences among groups, or two-tailed Student's t-test, on logic-transformed data. The cell culture data are reported with the number of replicate dishes in a single experiment, and each experiment was repeated independently at least twice with similar results. Significance was accepted at $P<0.05$.

Results

5-HT Induces PTHrP During Lactation. We examined PTHrP levels in mammary glands of TPH1 knockout (TPH1$^{-/-}$) mice and their corresponding normal controls (TPH1$^{-/-}$) at mid-lactation by immunostaining. In the mammary tissue in control mice (TPH1$^{-/-}$), PTHrP was detected both in the cytoplasm of the secretory cells, and within the secretory deposits in the alveolar lumens (left panel). Staining was observed in occasional cells that bordered the luminal epithelium, which were most likely to be myoepithelium. PTHrP immunoreactivity was markedly less in the glands of TPH lactating mice (right panel).

PTHrP was below the level of detectability in the blood plasma of non-lactating females, and was readily detectable during lactation The conversion of L-tryptophan to 5-hydroxytryptophan (5-HTP) is the rate-limiting step in 5-HT synthesis; therefore we injected 5-HTP to bypass the enzyme deficiency in TPH1 mice, and measured PTHrP plasma levels. The mice rescued with 5-HTP showed a time-dependent increase in plasma PTHrP($P<0.0001$, $R=0.92$), demonstrating that TPH1 activity was necessary for PTHrP secretion during lactation.

To determine whether PTHrP expression in mammary epithelial cells was directly responsive to 5-HT two cell models of lactogenic mammary epithelium were studied: lactogen-treated rodent HC11 cells, and primary bovine mammary epithelial cells embedded in floating collagen gels. In these models 5-HT induced PTHrP gene expression by 8-fold and 20-fold, respectively.

Figure 1:
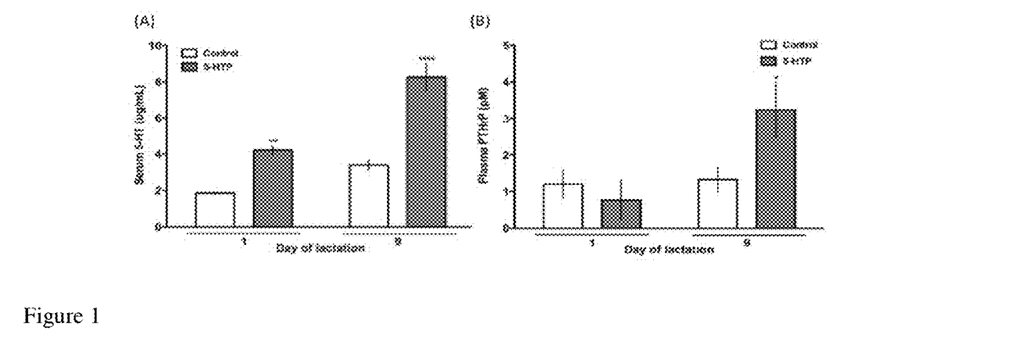
FIG. 1 depicts the circulating levels of (A) serum 5-HT and (B) plasma PTHrP in rats fed 0.2% 5-HTP from d13 pregnancy through d9 lactation compared to rats fed a control breeder diet.

Based on the foregoing results, studies were conducted to establish, in practice, that feeding a diet supplemented with 5-HTP would elevate circulating levels of serotonin (5-HT) and PTHrP. Rats were fed a diet supplemented with 0.2% 5-HTP, and circulating levels of 5-HT (serum) and PTHrP (plasma) in the rats fed 0.2% 5-HTP from d13 pregnancy through d9 lactation were compared to rats fed a control breeder diet. The 5-HTP supplemented diet resulted in elevation of 5-HT, and subsequently, elevation of PTHrP (see FIG. 1)

Figure 2:
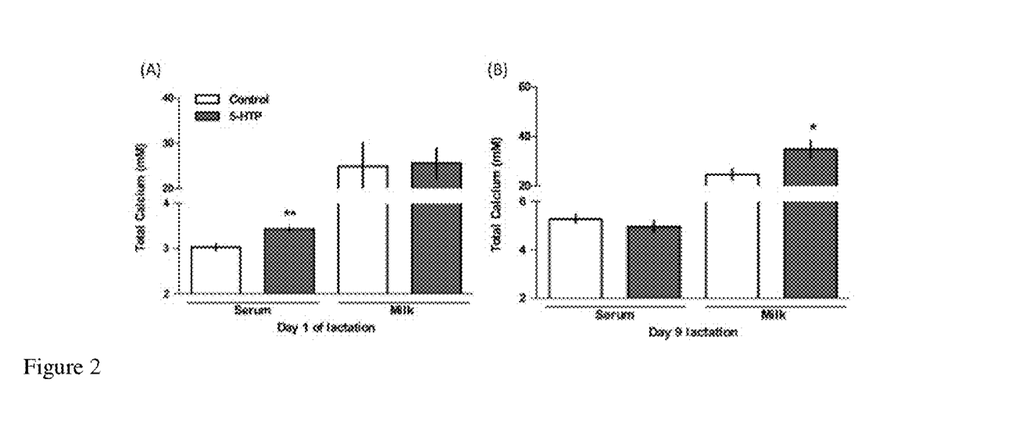
FIG. 2 depicts the serum and milk calcium concentrations in rats fed 0.2% 5-HTP (n=15) from d13 pregnancy-d9 lactation compared to rats fed a control (n=15) breeder diet at (A) day 1 of lactation and (B) day 9 of lactation.

Based on the foregoing results, studies were conducted to establish, in practice, that feeding a diet supplemented with 5-HTP would elevate circulating calcium levels in lactating animals. Serum and milk calcium concentrations were measured in rats fed a diet supplemented with 0.2% 5-HTP (n=15) from d13 pregnancy-d9 lactation, compared to rats fed a control (n=15) diet. Serum calcium concentrations were elevated by 5-HTP supplementation on dl of lactation, and subsequently, milk calcium levels were elevated by 5-HTP on d9 of lactation (FIG. 2).

REFERENCES

1. Akech J, Wixted J J, Bedard K, van der Deen M, Hussain S, Guise T A, van Wijnen A J, Stein J L, Languino L R, Altieri D C, Pratap J, Keller E, Stein G S and Lian J B. Runx2 association with progression of prostate cancer in patients: mechanisms mediating bone osteolysis and osteoblastic metastatic lesions. Oncogene 29: 6: 811-821, 2010.

2. Ardeshirpour L, Dann P, Adams D J, Nelson T, Van-Houten J, Horowitz M C and Wysolmerski J J. Weaning triggers a decrease in receptor activator of nuclear factor-kappaB ligand expression, widespread osteoclast apoptosis, and rapid recovery of bone mass after lactation in mice. Endocrinology 148: 8: 3875-3886, 2007.

3. Bliziotes M. Update in serotonin and bone. J, Clin. Endocrino/.Metab. 95: 9: 4124-4132, 2010.

4. Bostwick J R, Guthrie S K and Ellingrod V L. Antipsychotic-induced hyperprolactinemia. Pharmacotherapy 29: 1: 64-73, 2009.

5. Broadus A E, Mangin M, Ikeda K, Insogna K L, Weir E C, Burtis W J and Stewart A F. Humoral hypercalcemia of cancer. Identification of a novel parathyroid hormone-like peptide. N. Engl. J. Med. 319:9: 556-563, 1988.

6. Caplan R H, Wickus G G, Sloane K and Silva P D. Serum parathyroid hormone-related protein levels during lactation. J. Reprod. Med. 40: 3: 216-218, 1995.

7. Clines G A and Guise T A. Molecular mechanisms and treatment of bone metastasis. Expert Rev, Mol. Med. 10: e7, 2008.

8. DeMauro S and Wysolmerski J. Hypercalcemia in breast cancer: an echo of bone mobilization during lactation? J. Mammary Gland Biol. Neoplasia 10: 2: 157-167, 2005.

9. Dobnig H, Kainer F, Stepan V, Winter R, Lipp R, Schaffer M, Kahr A, Nocnik S, Patterer G and Leb G, Elevated parathyroid hormone-related peptide levels after human gestation: relationship to changes in bone and mineral metabolism. J. Clin. Endocrinol. Metab, 80: 12: 3699-3707, 1995, 10. Fiaschi-Taesch N M and Stewart A F. Minireview: parathyroid hormone-related protein as an intracrine factor—trafficking mechanisms and functional consequences. Endocrinology 144: 2: 407-411, 2003.

11. Franceschi R T, Xiao G, Jiang D, Gopalakrishnan R, Yang S and Reith K. Multiple signaling pathways converge on the Cbfa1/Runx2 transcription factor to regulate osteoblast differentiation. Connect. Tissue Res. 44 Suppl 1: 109-116, 2003.

12. Galli-Tsinopoulou A, Nousia-Arvanitakis S, Mitsiakos G, Karamouzis M and Dimitriadis A. Osteopenia in children and adolescents with hyperprolactinemia. J. Pediatr, Endocrinol. Metab. 13: 4: 439-441, 2000.

13. Graham T R, Agrawal K C and Abdel-Mageed A B. Independent and cooperative roles of tumor necrosis factor-alpha, nuclear factor-kappaB, and bone morphogenetic protein-2 in regulation of metastasis and osteomimicry of prostate cancer cells and differentiation and mineralization of MC3T3-E1 osteoblast-like cells. Cancer. Sct. 101: 1: 103-111, 2010.

14. Guo Y, Tiedemann K, Khalil J A, Russo C, Siegel P M and Komarova S V. Osteoclast precursors acquire sensitivity to breast cancer derived factors early in differentiation. Bone 43: 2: 386-393, 2008.

15. Hernandez L L, Limesand S W, Collier J L, Horseman N D and Collier R J. The bovine mammary gland expresses multiple functional isoforms of serotonin receptors. J Endocrinol. 203: 1: 123-131, 2009.

16. Horst R L, Goff J P and Reinhardt T A. Adapting to the transition between gestation and lactation: differences between rat, human and dairy cow. J. Mammary Gland Biol. Neopiasia 10:2: 141-156, 2005.

17. Hou X, Bailey J P, Vomachka A J, Matsuda M, Lockefeer J A and Horseman N D. Glycosylation-dependent cell adhesion molecule 1 (GlyCAM 1) is induced by prolactin and suppressed by progesterone in mammary epithelium. 141: 11:4278-83, 2000.

18. Huang W, Yang S, Shao J and Li Y P. Signaling and transcriptional regulation in osteoblast commitment and differentiation. Front. Biosci. 12: 3068-3092, 2007.

19. Inman C K and Shore P. The osteoblast transcription factor Runx2 is expressed in mammary epithelial cells and mediates osteopontin expression. J. Biol. Chem. 278: 49: 48684-48689, 2003.

20. Jackson J C, Cross R J, Walker R F, Markesbery W R, Brooks W H and Roszman T L. Influence of serotonin on the immune response. Immunology 54: 3: 505-512, 1985.

21. Kim H J, Kim J H, Bae S C, Choi J Y, Kim H J and Ryoo H M. The protein kinase C pathway plays a central role in the fibroblast growth factor-stimulated expression and transactivation activity of Runx2. J. Biol. Chem. 278: 1: 319-326, 2003.

22. Kingsley L A, Fournier P G, Chirgwin J M and Guise T A. Molecular biology of bone metastasis. Mol. Cancer. Ther. 6: 10: 2609-2617, 2007.

23. Klein M, Weryha G, Dousset B, Aubert V, Kaminsky P and Leclere J. Physiological role of PTHrP. Ann. Endocrinol. (Paris) 56: 3: 193-204, 1995.

24. Komori T. Regulation of bone development and maintenance by Runx2. Front. Biosci, 13: 898-903, 2008.

25. Kovacs C S. Calcium and bone metabolism during pregnancy and lactation. J. Mammary Gland Biol. Neopiasia 10:2: 105-118, 2005.

26. Kovacs C S and Chik C L. Hyperprolactinemia caused by lactation and pituitary adenomas is associated with altered serum calcium, phosphate, parathyroid hormone (PTH), and PTH-related peptide levels. J. Clin. Endocrinol. Metab. 80: 10: 3036-3042, 1995.

27. Liao J and McCauley L K. Skeletal metastasis: Established and emerging roles of parathyroid hormone related protein (PTHrP). Cancer Metastasis Rev. 25: 4: 559-571, 2006.

28. Luparello C, Santamaria F and Schilling T. Regulation of PTHrP and PTH/PTHrP receptor by extracellular Ca2+ concentration and hormones in the breast cancer cell line 8701-BC. Biol. Chem. 381:4: 303.308, 2000.

29. Marshall A M, Nommsen-Rivers L A, Hernandez L L, Dewey K G, Chantry C J, Gregerson K A and Horseman N D. Serotonin transport and metabolism in the mammary gland modulates secretory activation and involution. J. Clin. Endocrinol. Metab. 95: 2: 837-846, 2010.

30. Matsuda M, Imaoka T, Vomachka A J, Gudelsky G A, Hou Z, Mistry M, Bailey J P, Nieport K M, Walther D J, Bader M and Horseman N D. Serotonin regulates mammary gland development via an autocrine.paracrine loop. Dev. Cell. 6: 2: 193-203, 2004.

31. McGrath M F. A novel system for mammary epithelial cell culture. J. Dairy Sci. 70: 9: 1967-1980, 1987.

32. Misra M, Papakostas GI and Klibanski A. Effects of psychiatric disorders and psychotropic medications on prolactin and bone metabolism. J, Clin. Psychiatry 65: 12: 1607-18; quiz 1590, 1760-1, 2004.

33. Mundy G R. Metastasis to bone: causes, consequences and therapeutic opportunities. Naf. Rev. Cancer. 2; 8: 584-593, 2002.

34. Murray R D, Horsfield J E, McCormick W D, Williams H J and Ward D. Historical and current perspectives on the treatment, control and pathogenesis of milk fever in dairy cattle. Vet. Rec. 163: 19: 561-565, 2008.

35. Pai V P and Horseman N D. Regulation of epithelial turnover by serotonin through induction of cell loss. PLoS One 6: 2: e17028, 2011.

36. Pai V P and Horseman N D. Biphasic regulation of mammary epithelial resistance by serotonin through activation of multiple pathways. J Biol. Chem. 283:45:30901-30910, 2008.

37, Pai V P, Marshall A M, Hernandez L L, Buckley A R and Horseman N D. Altered serotonin physiology in human breast cancers favors paradoxical growth and cell survival. Breast Cancer Res. 11:6: R81, 2009.

38. Pai V P and Marshall A M. Intraluminal volume homeostasis: A common serotonergic mechanism among diverse epithelia. Communicative Integrative Biology 4:5: 0-1, 2011.

39. Pirola C J, Wang H M, Kamyar A, Wu S, Enomoto H, Sharifi B, Forrester J S, Clemens T L and Fagin J A. Angiotensin II regulates parathyroid hormone-related protein expression in cultured rat aortic smooth muscle cells through transcriptional and post-transcriptional mechanisms. J. Biol. Chem, 268: 3: 1987-1994, 1993, 40. Pratap J, Javed A, Languino L R, van Wijnen A J, Stein J L, Stein G S and Lian J B. The Runx2 osteogenic transcription factor regulates matrix metalloproteinase 9 in bone metastatic cancer cells and controls cell invasion. Mol. Cell. Biol. 25: 19: 8581-8591, 2005.

41. Rankin W, Grill V and Martin T J. Parathyroid hormone-related protein and hypercalcemia. Cancer 80: 8 Suppl: 1564-1571, 1997.

42. Richard V, Rosol T J and Foley J. PTHrP gene expression in cancer: do all paths lead to Ets? Clin. Rev. Eukaryot. Gene Expt. 15:2: 115-132, 2005.

43. Shibli-Rahhal A and Schlechte J. The effects of hyperprolactinemia on bone and fat. Pituitary 12: 2: 96.104, 2009.

44. Shore P. A role for Runx2 in normal mammary gland and breast cancer bone metastasis. J. Cell. Biochem. 96: 3: 484-489, 2005.

45. Sowers M F, Hollis B W, Shapiro B, Randolph J, Janney C A, Zhang D, Schork A, Crutchfield M, Stanczyk F and Russell-Aulet M. Elevated parathyroid hormone-related peptide associated with lactation and bone density loss. JAM4 276: 7; 549-554, 1996.

46. Stewart A F. Hyperparathyroidism, humoral hypercalcemia of malignancy, and the anabolic actions of parathyroid hormone and parathyroid hormone-related protein on the skeleton. J Bone Miner. Res. 17: 5: 758.762, 2002.

47. Stiegler C, Leb G, Kleinert R, Warnkross H, Ramschak-Schwarzer S, Lipp R, Clarici G, Krejs G J and Dobnig H. Plasma levels of parathyroid hormone-related peptide are elevated in hyperprolactinemia and correlated to bone density status. J, Bone Minev. Res. 10: 5: 751-759, 1995.

48. Stull M A, Pai V, Vomachka A J, Marshall A M, Jacob G A and Horseman N D. Mammary gland homeostasis employs serotonergic regulation of epithelial tight junctions. Proc. Natl. Acad. Sci, USA, 104: 42: 16708-16713, 2007.

49. Tai C J, Wu A T, Chiou J F, Jan H J, Wei H J, Hsu C H, Lin C T, Chiu W T, Wu C W, Lee H M and Deng W P. The investigation of mitogen-activated protein kinase phosphatase-1 as a potential pharmacological target in non-small cell lung carcinomas, assisted by non-invasive molecular imaging. BMC Cancer 10: 95, 2010.

50. Thiede M A. Parathyroid hormone-related protein: a regulated calcium-mobilizing product of the mammary gland. J. Dairy Sci. 77: 7: 1952-1963, 1994.

51. Thiede M A and Rodan G A. Expression of a calcium-mobilizing parathyroid hormone-like peptide in lactating mammary tissue. Science 242: 4876: 278-280, 1988.

52. Uemura H, Yasui T, Umino Y, Yamada M, Kuwahara A, Matsuzaki T, Maegawa M and Irahara M. Regulatory factors on parathyroid hormone-related peptide production by primary culture of lactating rat mammary gland. 37: 8: 463-467, 2005.

53. van der Deen M, Akech J, Wang T, FitzGerald T J, Altieri D C, Languino L R, Lian J B, van Wijnen A J, Stein J L and Stein G S. The cancer-related Runx2 protein enhances cell growth and responses to androgen and TGF-beta in prostate cancer cells. J. Cell. Biochem. 109:4: 828-837, 2010.

54. VanHouten J N, Dann P, Stewart A F, Watson C J, Pollak M, Karaplis A C and Wysolmerski J J. Mammary-specific deletion of parathyroid hormone-related protein preserves bone mass during lactation. J. Clin. Invest. 112:9; 1429-1436, 2003.

55. Wysolmerski J J. Interactions between breast, bone, and brain regulate mineral and skeletal metabolism during lactation. Ann. NY Acad Sci, 1192:1:161-169, 2010.

56. Ye Y, Falzon M, Seitz P K and Cooper C W. Overexpression of parathyroid hormone-related protein promotes cell growth in the rat intestinal cell line IEC-6. Regul. Pept. 99: 2-3: 169-174, 2001.

All publications, patents and patent applications cited herein, whether supra or infra, are hereby incorporated by reference in their entirety to the same extent as if each individual publication, patent or patent application was specifically and individually indicated as incorporated by reference. It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein, will only be incorporated to the extent that no conflict arises between that incorporated material and the existing disclosure material.

It must be noted that, as used in this specification and the appended claims, the singular forms "a," "an" and "the" include plural referents unless the content clearly dictates otherwise. Thus, for example, reference to a "colorant agent" includes two or more such agents.

Unless defined otherwise, all technical and scientific terms used herein have the same meaning as commonly understood by one of ordinary skill in the art to which the invention pertains. Although a number of methods and materials similar or equivalent to those described herein can be used in the practice of the present invention, the preferred materials and methods are described herein.

While it is apparent that the illustrative embodiments of the invention herein disclosed fulfill the objectives stated above, it will be appreciated that numerous modifications and other embodiments may be devised by one of ordinary skill in the art. Accordingly, it will be understood that the appended claims are intended to cover all such modifications and embodiments, which come within the spirit and scope of the present invention.

It should be noted that, when employed in the present disclosure, the terms "comprises," "comprising," and other derivatives from the root term "comprise" are intended to be open-ended terms that specify the presence of any stated features, elements, integers, steps, or components, and are not intended to preclude the presence or addition of one or more other features, elements, integers, steps, components, or groups thereof.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

What is claimed is:

1. A method for the prevention and/or treatment of periparturient hypocalcemia (milk fever) in lactating female mammals, the method comprising administering to a female mammal in need of such treatment a therapeutically effective amount of a pharmaceutical agent that increases serotonergic signaling wherein the pharmaceutical agent is administered at the onset of lactation.

2. The method of claim 1, wherein the lactating female mammal is selected from the group consisting of bovine, ovine, porcine, avian and humans.

3. The method of claim 1, wherein the administration of the agent improves calcium mobilization of the lactating mammal.

4. The method of claim 1, wherein the pharmaceutical agent comprises 1-95 wt % serotonin agonist.

5. The method of claim 1, wherein the pharmaceutical agent comprises 5-30 wt % serotonin agonist.

6. The method of claim 1, wherein the effective daily dosages of 5-HTP range between about 5 mg and about 10,000 mg.

7. The method of claim 1, wherein the effective daily dosages of 5-HTP range between about 25 mg to about 2500 mg.

8. The method of claim 1, wherein the pharmaceutical agent is administered in an amount of approximately 50 mg/kg to 500 mg/kg.

9. The method of claim 1, wherein the pharmaceutical agent is administered in a sustained-release formulation.

10. The method of claim 1, wherein the pharmaceutical agent is administered to the mammal until at least day 4 of the treatment.

11. The method of claim 1, wherein the pharmaceutical agent is administered to the mammal until at least day 10 of the treatment.

12. The method of claim 1, wherein the pharmaceutical agent is administered as a rumen-protected formulation.

13. The method of claim 1, wherein the pharmaceutical agent administration causes an overall increase in ruminant serum calcium concentration in the periparturient period.

14. The method of claim 1, further comprising the steps of producing a final feed by mixing a composition containing serotonin agonist or a salt thereof and a stabilizer with a suitable premix, which is a component of the final feed.

15. A method for maintaining calcium homeostasis in periparturient female mammals, the method comprising treating the female mammal with an effective amount of a pharmaceutical agent that increases serotonergic signaling wherein the pharmaceutical agent is administered at the onset of lactation wherein the said pharmaceutical agent is 5-HTP.

16. The method of claim 15, wherein the pharmaceutical agent increases PTHrP levels.

17. The method of claim 15, wherein 5-HTP is used in the manufacture of a medicament to increase calcium mobilization in a ruminant animal.

18. The method of claim 15, wherein 5-HTP is used in the manufacture of a medicament to increase lactation in a ruminant animal.

19. The method of claim 15, wherein 5-HTP is used in the manufacture of a medicament for the palliative, prophylactic or curative treatment of ruminant diseases associated with reduced calcium concentrations.

* * * * *

UNITED STATES PATENT AND TRADEMARK OFFICE
CERTIFICATE OF CORRECTION

Page 1 of 1

PATENT NO. : 9,585,870 B2
APPLICATION NO. : 14/375103
DATED : March 7, 2017
INVENTOR(S) : Nelson D. Horseman and Laura Hernandez Baumgard It is certified that error appears in the above-identified patent and that said Letters Patent is hereby corrected as shown below:

In the Specification

Under GOVERNMENT INTEREST:
Column 1, Line 21; Replace "The government may have certain rights in the invention" with --The government has certain rights in this invention--

Signed and Sealed this
Third Day of January, 2023

Katherine Kelly Vidal
*Director of the United States Patent and Trademark Office*